United States Patent [19]
Lavore

[11] Patent Number: 5,826,841
[45] Date of Patent: Oct. 27, 1998

[54] THERAPEUTIC ELBOW SUPPORT SYSTEM

[76] Inventor: Joseph S. Lavore, 6492 Sugar Tree Dr., Spring Hill, Fla. 34607

[21] Appl. No.: 819,287

[22] Filed: Mar. 18, 1997

[51] Int. Cl.$^6$ ........................................................ A61F 7/00
[52] U.S. Cl. ............................................ 248/118; 607/111
[58] Field of Search ................................ 248/118, 118.1, 248/118.3, 118.5; 400/715; 607/111, 114

[56] References Cited

U.S. PATENT DOCUMENTS

| | | | |
|---|---|---|---|
| 4,621,781 | 11/1986 | Springer | 248/118 |
| 5,072,905 | 12/1991 | Hyatt | 248/118 |
| 5,125,606 | 6/1992 | Cassano et al. | 248/118 |
| 5,158,255 | 10/1992 | Fuller | 248/118 |
| 5,163,646 | 11/1992 | Engelhardt | 248/118 |
| 5,183,230 | 2/1993 | Walker et al. | 248/118 |
| 5,242,139 | 9/1993 | Aldrich | 248/118 |
| 5,356,099 | 10/1994 | Sereboff | 248/118.1 |
| 5,374,018 | 12/1994 | Daneshvar | 248/118 |
| 5,383,921 | 1/1995 | Barry | 607/114 |
| 5,385,322 | 1/1995 | Kim et al. | 248/118 |
| 5,435,508 | 7/1995 | Deuitch et al. | 248/118 |
| 5,445,349 | 8/1995 | Hart | 248/118 |
| 5,456,704 | 10/1995 | Kilcullen | 607/114 |
| 5,476,491 | 12/1995 | Mayn | 607/111 |
| 5,513,824 | 5/1996 | Leavitt et al. | 248/918 X |
| 5,566,913 | 10/1996 | Prokop | 248/118 |
| 5,568,907 | 10/1996 | Wolfe et al. | 248/118 |
| 5,572,941 | 11/1996 | Arnos | 400/715 X |
| 5,601,264 | 2/1997 | Peart | 248/118.1 |
| 5,628,483 | 5/1997 | Smith et al. | 248/118 |

OTHER PUBLICATIONS

Hydrowrest, P.C.M.E.D., Inc.

*Primary Examiner*—Ramon O. Ramirez
*Assistant Examiner*—Long Dinh Phan
*Attorney, Agent, or Firm*—Dorothy S. Morse

[57] ABSTRACT

A prevention and therapeutic support system for body parts susceptible to repetitive strain injury comprising an assembly having a centrally located gel-pack sandwiched between, upper and lower foam layers each having downwardly depending perimeter edges which when placed adjacent to one another form a cavity into which the gel-pack can be placed, the foam layers to to completely encompassing the gel-pack during use, the gel-pack substantially filling the cavity, the gel-pack and foam layers being placed into an outer covering into which maintains the foam in its optimal position around the gel-pack during use, the outer envelope has an opening through which the foam layer and gel-pack can be moved for independent heating and cooling of the gel-pack, the gel-pack being capable of being both heated and chilled, the viscous non-hardening gel material in the gel-pack being able to maintain hot and cold temperatures for extended periods of time. Applications may include, but are not limited to, use to prevent and treat cumulative trauma, such as the pain, muscle spasm, and inflammation of joints associated with the repetitive strain injury experienced by nail technicians in their elbows after several hours of work.

17 Claims, 1 Drawing Sheet

THERAPEUTIC ELBOW SUPPORT SYSTEM

BACKGROUND

1. Field of Invention

This invention relates to support devices for the prevention treatment of repetitive strain injuries, specifically to a prevention and therapeutic support system for body parts susceptible to repetitive strain injury, comprising a four piece assembly consisting of gel-pack sandwiched between an upper foam layer and a lower foam layer, and an outer envelope of non-abrading material into which the gel-pack and foam layer sandwich is positioned during its support of a body part such as the elbow of a nail technician. The foam layers each have an extended perimeter edge which when positioned against the other extended perimeter edge forms a cavity therebetween the gel-pack substantially filling the cavity, and the foam layers substantially filling the outer envelope so that the gel-pack will be optimally retained under the supported body part during prolonged use. The outer envelope also has an opening therethrough of sufficient dimension for easy access to removal of the the gel-pack and foam layers so that the gel-pack can be separated from the foam layers for individual heating in a microwave oven or chilling in a freezer the gel-pack comprising a viscous non-hardening gel substance able to maintain hot and cold temperatures for extended periods of time. Applications may include, but are not limited to, use in preventing and treating cumulative trauma, such as the pain, muscle spasm, and inflammation of joints associated with the repetitive strain injury experienced by nail technicians in their elbows after several hours of professional work.

2. Description of Prior Art

The number of people suffering from repetitive strain injury has continually increased, so much so that repetitive strain injury has recently surpassed back pain as a leading cause of disability. The widespread use of the computer mouse and computer keyboards, and the need of mouse and keyboard operators to maintain their hands in relatively unvarying positions for extended periods of time during such use, is largely responsible for the noted increase in repetitive strain injury disability. However, nail technicians and others also experience elbow pain as a result of the unvarying hand and arm positions they must use to perform their work functions. The present invention provides both preventative and therapeutic relief to such persons by providing a non-abrading cushioned surface that substantially maintains its shape during prolonged use so that it can evenly distribute the downward pressure exerted by the body part it supports during the entire period of its use. The advantages of the present invention over known prior art is that the present invention is able to provide a removable non-hardening viscous core which can be expediently and repeatedly heated or chilled in combination with upper and lower foam layers which define a space within which the centrally located gel-pack must be confined during use. Thus, even if the upper foam layer becomes somewhat compressed during prolonged use, the gel-pack would maintain a sufficient depth dimension and configuration for continued even support of a body part of the present invention positioned upon it since the foam layers would not allow the viscous gel to move laterally away from its contact point with the body part needing support. It is contemplated for the four-piece assembly to have a variety of sizes, shapes, and thicknesses dimensions to satisfy the support needs of differing body parts.

Several wrist supports for computer keyboard operators are known which comprise foam padding or gel. However, all known prior art supports have one or more disadvantages which do not allow them to function as effectively as the present invention in support of other body parts. Wrist supports for keyboard operator use must only support a portion of the weight of the attached operator hand and arm, since during use the operator's arm is generally placed in a horizontal position and the operator's shoulders support much of the weight load. In contrast, when supporting an elbow, the present invention must have sufficient thickness dimension and resiliency to evenly support the entire weight of the user's arm, a portion of the user's shoulder and upper body, as well as anything the user may be holding in his or her hand. The invention in U.S. Pat. No. 5,385,322 to Kim (1995) discloses an elbow rest which clamps to the edge of a work surface and helps an operator maintain a fatigue-resistant posture. The Kim invention also helps to steady the operator's hands. However, the Kim invention contemplates only a self-skinned foam polymer pad to support a worker's elbows, and its function is preventative, not therapeutic. It is not known in this field to have a system for the support of body parts susceptible to repetitive strain injury comprising a four-piece assembly having a gel-pack sandwiched between upper and lower foam layers and an envelope of non-abrading material into which the gel-pack and foam layer sandwich is positioned during use, with the gel-pack substantially filling a cavity formed between the foam layers and the foam layers substantially filling the outer envelope into which they are inserted for optimal retention of the gel-pack beneath the supported body part during prolonged use, the gel-pack being separable from the foam layers and envelope, capable of being repeatedly bested and chilled, and able to maintain hot and cold temperatures for extended periods of time.

SUMMARY OF INVENTION

Objects and Advantages

It is the primary object of this invention to provide a prevention and therapeutic device for the repetitive strain injury experienced by nail technicians in their elbows after several hours of professional work. A further object of this invention is to provide a prevention and therapeutic device for body parts susceptible to repetitive strain injury which uses a viscous core of gel that does not harden upon chilling to ensure that even pressure will be applied to the supported body parts under all temperature condition. It is also an object of this invention to provide a therapeutic device which can be repeatedly heated or chilled for use reducing the pain, muscle spasm, and inflammation of joints which results from repetitive strain injury. A further object of this invention is to provide a prevention and therapeutic device for body parts susceptible to repetitive strain injury which is made from materials which can withstand repeated heating in a microwave oven and repeated chilling in a freezer without rupture for convenient workplace use. It is also an object of this invention to provide a prevention and therapeutic device for body parts susceptible to repetitive strain injury which has structure that allows a wide range of configurations and dimensions. A further object of this invention is to provide a prevention and therapeutic device for body parts susceptible to repetitive strain injury which has a removable gel-pack so that the gel-pack can be more quickly heated and chilled than if it remained surrounded by its foam layer support structure, and so that the cleanliness of the outer envelope can be more easily maintained.

As described herein, properly manufactured and used, the present invention would provide a preventative and therapeutic sandwiched gel and foam support assembly for use with body parts susceptible to repetitive strain injury, such as the elbow of a nail technician. The foam layers would each have downwardly depending perimeter edges so that when the foam layer edges are placed against one another, they form a cavity to completely encompasses and supports the viscous gel core. It is contemplated for the cavity that gel-pack to be nearly identical in size to the cavity so that the gel-pack substantially fills it. The centrally positioned gel-pack is made from a non-hardening viscous gel material which can be repeatedly heated and chilled, and which can be chilled in a freezer without becoming rigid. It is also contemplated for the gel-pack to be able to withstand heating in a microwave oven, or other heating device, without rupture so that the present invention can be conveniently used in the workplace. The combination of two foam layers supporting a central gel core better distributes the pressures applied to a user's body parts when the body parts must remain in a substantially unvarying position during prolonged periods of time. The combination of gel and foam provides better cushioning than a gel core alone which can either be too inflexible or too resilient depending on the amount of gel placed into the envelope designed to contain it. Also, the combination of gel and foam provides for better cushioning than one or more foam layers which can become compressed during prolonged periods of use. The present invention also has an outer envelope made from washable material which has an opening therethrough to allow the gel-pack to be easily removed for rapid heating or chilling prior to therapeutic use. It is contemplated for the viscous core of the present invention to be heated for therapeutic relief from pain resulting from chronic repetitive strain injury and chilled for preventative treatment, as well as for treatment of acute symptoms, including pain, muscle spasm, and inflammation of joints, occurring as a result of new or renewed repetitive strain injury. It is also contemplated for the sandwiched structure of the present invention to be made into devices of differing surface dimension and thickness for different body part support needs. Although not critical and not limited thereto, it is contemplated for commonly used sizes of the present invention to include those having a rectangular configuration with width and length dimensions ranging between approximately three inches by three inches square and, approximately six inches square, such as that proposed by six inches for nail technician use.

The description herein provides preferred embodiments of the present invention but should not be construed as limiting the scope of the present repetitive strain injury prevention and treatment device. For example, variations in the length, width, and height dimensions of the gel-pack, the length, width, and height dimensions of each of the foam layers which does not have to be identical in thickness to the other foam layer, the type of foam material used as long as it is sufficiently resilient to resist compression and recover its original shape promptly after being compressed, the rigidity of the foam material used, the type of gel used as long as it will not harden when chilled and as long as it is non-toxic in the event of accidental rupture, the type of non-abrasive material used for the outer envelope, and the type of fastening means used to close the opening in the outer envelope which allows easy removal of the gel-pack therefrom for heating and chilling, other than those shown and described herein, may be incorporated into the present invention. Thus the scope of the present invention should be determined by the appended claims and their legal equivalents, rather than the examples given.

DETAILED DESCRIPTION OF PREFERRED EMBODIMENTS

Figure 1:
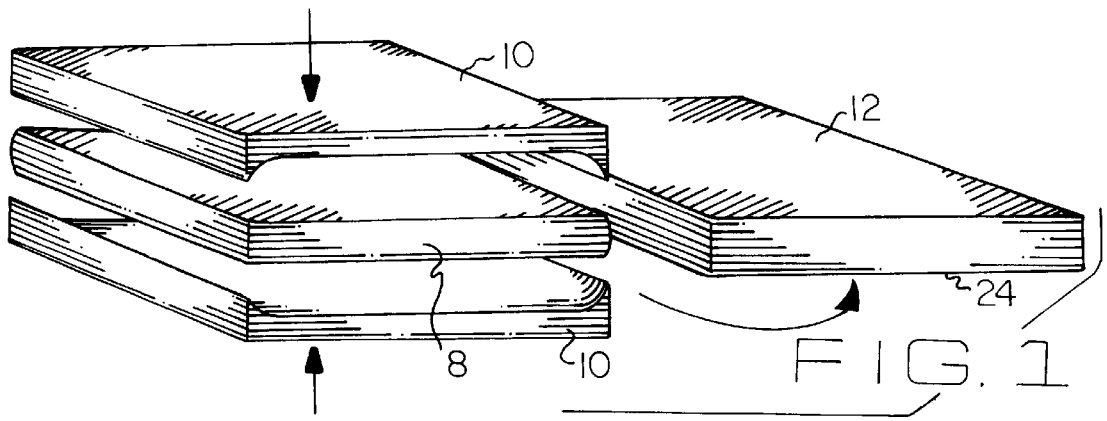
FIG. 1 is a perspective view of the invention having an outer envelope with two foam layers and a centrally positioned gel-pack positioned for insertion through a hidden opening in the back surface of outer envelope.

FIG. 1 shows repetitive strain injury prevention and therapeutic device 2 having an outer envelope 12, two foam layers 10, and a centrally located gel-pack 8. Foam layers 10 each have a perimeter with downwardly depending edges for defining an interior cavity within which to encompass gel-pack 8 during use. FIG. 1 shows gel-pack 8 sandwiched between the two foam layers 10 and positioned for insertion into envelope 12 through an opening, shown as number 6 in FIG. 2, through back surface 24 of covering 12. The height of the upper and lower foam layers 10 is not critical, and it is contemplated for them to have the same height dimension, or different height dimensions depending upon the use required. Also not critical is the type of foam material to be used for foam layers 10, as long as it is sufficiently resilient to resist compression and recover its original shape promptly after being compressed. Further, it is contemplated to have differing amounts of gel material within gel-pack 8, the thickness of gel-pack 8 during use being determined by the configuration of foam layers 10.

Figure 2:
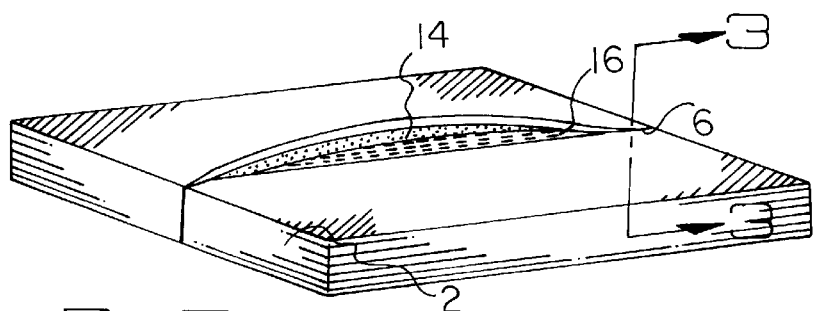
FIG. 2 is a perspective view of the bottom surface of the invention showing an opening therein for use in insertion and removal of the foam layers and the gel-pack from the outer envelope.
Figure 3:
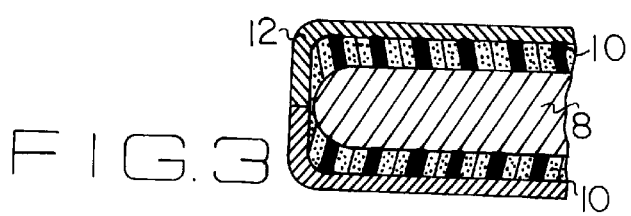
FIG. 3 is a sectional view of the invention having foam layers and a gel-pack positioned within an envelope covering.
Figure 4:
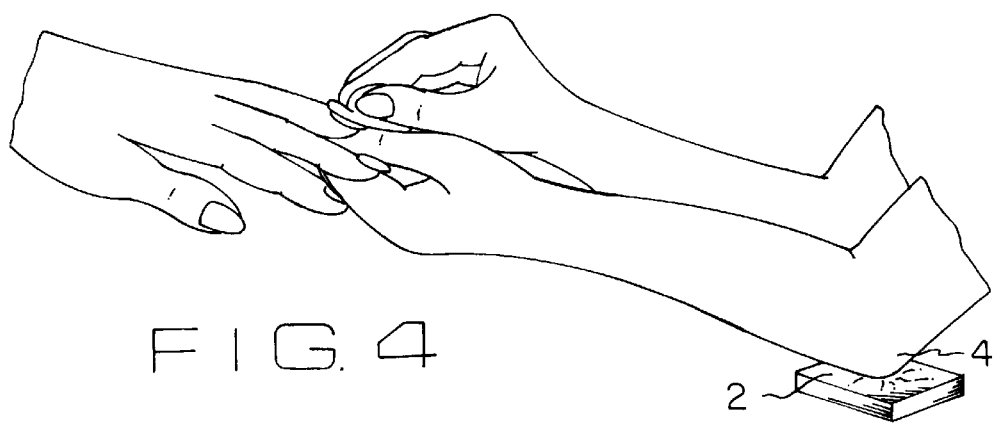
FIG. 4 is a perspective view of the invention in use supporting a human elbow.

FIG. 2 shows repetitive strain injury prevention and treatment device 2 having opening 6 therethrough, with opening 6 secured by hooking fasteners 14 and pile fasteners 16. In the preferred embodiment it is contemplated for opening 6 to be longitudinally oriented and to extend substantially the full length of envelope 12. Although the use of hooking fasteners 14 and pile fasteners 16 is preferred, it is also contemplated to have other means of closure for opening 6 in envelope 12. Opening 6 must be of sufficient size and dimension for foam layers 10 and gel-pack 8 to be easily inserted and removed from envelope 12. Although not shown and not critical to the present invention, it is contemplated for hooking fasteners 14 and pile fasteners 16 to he attached to envelope 12 by conventional means, such as stitching, and for the portion of envelope 12 adjacent to opening 6 to be secured to prevent unraveling of its fabric, again by stitching or other conventional means. FIG. 3 shows gel-pack 8 positioned between two foam layers 10 and the sandwiched gel-pack 8 and foam layers 10 being positioned within envelope 12. Envelope 12 has a dimension and configuration sufficient to completely contain gel-pack 8 and foam layers 10, with gel-pack 8 and foam layers 10 substantially filling covering 12 during use. FIGS. 1 and 3 show foam layers 10 having an arcuate inside surface adjacent to the proximal end of each downwardly depending perimeter edge. FIG. 4 shows repetitive strain injury prevention and therapeutic device 2 in use under a human elbow 4.

Although not critical to the present invention, it is contemplated for envelope 12 to be made from washable material. Also, hooking fasteners 14 and pile fasteners 16 can each be one continuous strip attached to opposite sides of opening 6, or several hooking fasteners 14 and one or more pile fasteners 16 can be attached adjacent to opening 6 to close it to retain gel-pack 8 and foam layers 10 within envelope 12. Also, although the type of gel used is not critical to the present invention as long as it can be chilled without hardening and as long as it can retain heat and cold for extended periods of time, it is contemplated for gel-pack 8 to be made from materials which can be heated in a microwave oven (not shown), or other heating device, and chilled in a freezer (not shown) without rupture. Further, the length of opening 6 is not critical to the present invention as long as gel-pack 8 and foam layers 10 can be easily inserted into, and removed from, envelope 12. Also, the foam used for foam layers 10 must be resilient, but at the same time have sufficient rigidity to be able to retain its shape during extended use.

A person using repetitive strain injury prevention and therapeutic device 2, would first remove gel-pack 8 and foam layers 10 from envelope 12 through opening 6. Then after separating gel-pack 8 from foam layers 10, the person would heat gel-pack 8 in a microwave oven (not shown) or other heating device, or in the alternative chill gel-pack 8 in a freezer (not shown), as needed. When sufficiently hot or cold, the person would then sandwich gel-pack 8 between both foam layers 10 so that the downwardly depending perimeter edges of foam layers 10 form a cavity into which gel-pack 8 is placed, gel-pack 8 substantially fills the cavity, and foam layers 10 completely surround gel-pack 8. The sandwiched gel-pack 8 and foam layers 10 would then be re-inserted through opening 6 into envelope 12 and positioned to substantially fill covering 12 so that envelope 12 maintains gel-pack 8 and foam layers 10 in their sandwiched configuration during use. Repetitive strain injury prevention and therapeutic device 2 would then be positioned directly under a body part subject to repetitive strain injury to support it. After gel-pack 8 reassumes room temperature, it can be removed from envelope 12, again heated or chilled depending upon the need of the person using it, and then reinserted into envelope 12 for continued use. Since gel-pack 8 can be heated in a microwave oven or chilled in a freezer, both appliances being commonly available in today's workplace, repetitive strain injury preventative and treatment device 2 can be easily used to treat and prevent repetitive strain injury in the workplace. Also, since covering 12 can be made from a wide variety of colored fabrics and those having decorative designs, the present invention is not unattractive for workplace use.

What is claimed is:

1. A repetitive strain injury prevention and therapeutic system capable of providing both elevated and cool temperatures to body parts which must be kept in unvarying positions for prolonged periods of time, said system comprising a four-piece assembly consisting of a gel-pack, an upper foam layers an outer envelope and a lower foam layer, each of said foam layers having perimeter edges downwardly depending therefrom, said perimeter edges being sufficiently sized so that when said perimeter edges from one of said foam layers are placed adjacent to said perimeter edges from the other of said foam layers said perimeter edges form a cavity slightly larger than said gel-pack, said gel-pack being positioned within said cavity and completely encompassed thereby during use with said gel-pack substantially filling said cavity, said outer envelope also having sufficient dimension to contain said gel-pack and said foam layers with said foam layers substantially filling said outer envelope, said outer envelope being made from non-abrading material and having an opening therethrough sized for convenient removal of said foam layers and said gel-pack so that said gel-pack can be independently heated and cooled for prevention and therapeutic use, said outer envelope also comprising fastening means adjacent to said opening for closing said opening sufficiently for secure retention of said foam layers and said gel-pack within said outer envelope during use, said gel-pack comprising a gel material capable of being both heated and chilled, said gel material being able to maintain hot and cold temperatures for extended periods of time, and said gel material being able to become chilled without becoming hardened so that said system can both prevent and treat cumulative trauma involving the pain, muscle spasm, and inflammation of joints associated with repetitive strain injury.

2. The system of claim 1 wherein said outer envelope has a lower surface, and wherein said opening is elongated and positioned longitudinally through said lower surface.

3. The system of claim 2 wherein said fastening means comprises at least one hooking fastener and at least one pile fastener.

4. The system of claim 1 wherein said perimeter edges each have a proximal end and said foam layers each have an inside arcuate surface adjacent to said proximal end.

5. The system of claim 1 wherein said gel-pack, said lower foam layer, and said upper foam layer have length and width dimensions of approximately six inches by six inches for use by a nail technician for protection of an elbow from repetitive strain injury.

6. The system of claim 1 wherein said outer envelope is made from washable material.

7. The system of claim 1 wherein said outer envelope is made from non-toxic materials able to withstand heating in a microwave oven without rupture.

8. The system of claim 1 wherein said outer envelope is made from non-toxic materials able to withstand chilling in a freezer without rupture.

9. The system of claim 1 wherein said foam layers are made from foam material which resists compression and recovers its original shape promptly after being compressed.

10. A method for both treating and preventing repetitive strain injury to body parts which results from said body parts being held in unvarying positions for prolonged periods of time, said method comprising the steps of providing a gel-pack which does not harden upon chilling and which will maintain heat and cold for extended periods of time, two foam layers, an envelope made of non-abrading material, and a plurality of fasteners; heating and chilling said gel-pack to temperatures sufficiently different from room temperature to provide relief to body parts susceptible to repetitive strain injury; forming one side of said foam layers to have downwardly depending perimeter edges; also forming said foam layers to have an arcuate inside surface adjacent to said perimeter edges; placing said foam layers in positions adjacent to one another to form a cavity therebetween; placing said gel-pack between said foam layers within said cavity so that said gel-pack substantially fills said cavity and said foam layers completely surround said gel-pack to form a gel-pack and foam layer assembly; forming an opening in said outer envelope; inserting said assembly through said opening; positioning said assembly within said outer envelope so that said assembly substantially fills said outer envelope and said outer envelope maintains said gel-pack and said foam layers as an assembly during use; using said fasteners to close said opening to retain said assembly within said outer envelope during use when said body parts exert downward pressure on said outer envelope; and positioning said outer envelope and retained assembly under a body part subject to repetitive strain injury to support said body part during activity which otherwise would subject said body part to repetitive strain injury.

11. The method of claim 10 wherein said step of forming said opening in said outer envelope further comprises the steps of making said opening an elongated opening and forming said opening longitudinally through said outer envelope.

12. The method of claim 10 wherein said step of providing said plurality of fasteners comprises the providing of a plurality of hook and pile fasteners.

13. The method of claim 10 wherein said step of providing said foam layers comprises the providing of foam layers having length and width dimensions of approximately six inches.

14. The method of claim 10 wherein said step of providing said outer envelope comprises the providing of an outer envelope made from washable material.

15. The method of claim 10 wherein said step of providing said gel-pack comprises the providing of a gel-pack made from non-toxic materials able to withstand heating in a microwave oven without rupture.

16. The method of claim 10 wherein said step of system of providing said gel-pack comprises the providing of a gel-pack made from non-toxic materials able to withstand chilling in a freezer without rupture.

17. The method of claim 10 wherein said step of providing said foam layers comprises the providing of foam layers made from foam material which resists compression and recovers its original shape promptly after being compressed.

* * * * *